United States Patent
Batiste

(10) Patent No.: US 12,186,465 B2
(45) Date of Patent: Jan. 7, 2025

(54) CATHETER CLEARANCE DEVICE AND METHOD OF USE

(71) Applicant: Stanley Batiste, Granite Bay, CA (US)

(72) Inventor: Stanley Batiste, Granite Bay, CA (US)

( * ) Notice: Subject to any disclaimer, the term of this patent is extended or adjusted under 35 U.S.C. 154(b) by 174 days.

(21) Appl. No.: 17/141,098

(22) Filed: Jan. 4, 2021

(65) Prior Publication Data

US 2021/0205523 A1    Jul. 8, 2021

Related U.S. Application Data

(60) Provisional application No. 62/957,088, filed on Jan. 3, 2020.

(51) Int. Cl.
| | |
|---|---|
| *A61M 1/28* | (2006.01) |
| *A61M 5/168* | (2006.01) |
| *A61M 25/00* | (2006.01) |
| *A61M 25/01* | (2006.01) |
| *A61M 60/37* | (2021.01) |
| *A61M 60/50* | (2021.01) |

(52) U.S. Cl.
CPC ........ *A61M 1/285* (2013.01); *A61M 5/16804* (2013.01); *A61M 5/16881* (2013.01); *A61M 2025/0073* (2013.01); *A61M 25/0108* (2013.01); *A61M 60/37* (2021.01); *A61M 60/50* (2021.01); *A61M 2205/32* (2013.01)

(58) Field of Classification Search
CPC .... A61M 1/285; A61M 1/281; A61M 60/279; A61M 60/37; A61M 60/50; A61M 25/0108; A61M 2025/0073; A61M 5/46
See application file for complete search history.

(56) References Cited

U.S. PATENT DOCUMENTS

| | | | | |
|---|---|---|---|---|
| 3,951,570 A | * | 4/1976 | De Biaggi | A61M 60/113 417/319 |
| 4,191,181 A | * | 3/1980 | Franetzki | A61M 5/172 604/151 |
| 4,704,102 A | * | 11/1987 | Guthery | A61M 25/1025 604/921 |
| 5,372,709 A | * | 12/1994 | Hood | A61M 1/362263 417/474 |
| 5,484,401 A | * | 1/1996 | Rodriguez | A61M 39/0606 604/28 |

(Continued)

FOREIGN PATENT DOCUMENTS

WO    WO-9717102 A1 *    5/1997    ........ A61M 25/0014

*Primary Examiner* — Nilay J Shah
(74) *Attorney, Agent, or Firm* — Weide & Miller, Ltd.

(57) ABSTRACT

A method and apparatus to direct a drug directly at the point needed for a specific duration for dialysis catheters which are made in standard sizes. Disclosed is a combination of a rate and duration-controlled infusion pump and reservoir and a pre-measured infusion catheter with a radiopaque distal tip. Along the length of the infusion catheter there is a luer lock connector and anti-leak valve. The invention is inserted into a dialysis catheter where the preset marking is aligned with the catheter hub and the distal infusion tip rest at or near the end of the dialysis catheter. The infusion unit is then activated, and the drug is delivered at the distal tip of the catheter, at or in the fibrin for maximum effect. The method of use and device saves time and resources as it can be deployed without the need for a surgical suite or heath care team.

12 Claims, 15 Drawing Sheets

(56) References Cited

U.S. PATENT DOCUMENTS

| | | | | |
|---|---|---|---|---|
| 5,620,312 | A | * | 4/1997 | Hyman ................. A61M 5/142 417/474 |
| 2004/0097880 | A1 | * | 5/2004 | Schur ................... A61M 29/00 977/875 |
| 2006/0173407 | A1 | * | 8/2006 | Shaughnessy .... A61M 25/0105 604/95.01 |
| 2011/0144620 | A1 | * | 6/2011 | Tal .................... A61M 25/0108 604/529 |
| 2012/0095537 | A1 | * | 4/2012 | Hall ....................... A61M 1/32 607/105 |
| 2015/0165110 | A1 | * | 6/2015 | Gopalakrishna ...... A61M 25/00 604/523 |
| 2017/0072125 | A1 | * | 3/2017 | Wallenås .............. A61M 1/282 |

* cited by examiner

CATHETER CLEARANCE DEVICE AND METHOD OF USE

BACKGROUND OF THE INVENTION

1. Field of Invention

The present invention relates to clearance of occluded catheters.

2. Description of Related Art

Patients with end stage renal disease ("ESRD") have lost their normal kidney function, and as a result require dialysis to substitute the function of the kidney cleansing the blood. ESRD affects almost 750,000 people per year in the United States. Hemodialysis requires that large volume blood access and exchange be consistently available to sustain the life of the patient. Medicare coverage is extended to a person of any age who requires either dialysis or transplantation to maintain life. The people who live with ESRD are 1% of the U.S. Medicare population but account for roughly 7% of the Medicare budget. Mortality rates vary depending on the ESRD treatment. After one year of treatment, those on dialysis have a 20-25% mortality rate, with a 5-year survival rate of 35%. Persons who receive transplants have a 3% mortality rate after 5 years. There are two types of dialysis, hemodialysis, and peritoneal dialysis. For purposes of this overview we will primarily be focused on hemodialysis.

Hemodialysis care costs the Medicare system an average of $90,000 per patient annually in the United States, for a total of $28 billion. Typically, a dialysis patient will require 3-4 hours of dialysis three days a week. The challenge with providing hemodialysis is maintaining access to large volumes of blood when a body constantly fights attempts to keep access available by healing closed such access. Currently there are three ways to provide hemodialysis; dialysis catheters, arterial venous fistulas (AVF's) and arterial venous grafts (AVGs). Although used worldwide, catheters are known not to be efficient for long term dialysis. Unfortunately, catheters have very short patency rates and high rates of infection greater than 60% of all dialysis patients use catheters.

Long term catheter patency rates remain low at less than 35% after 1 year and an average patency rate of 80 days. It is the development of a fibrin sheath that determines the long term patency of a catheter. This sheath, initially composed of fibrinogen, albumin, lipoproteins, and coagulation factors, begins to form within 24 hours of insertion. The fibrin sheath attracts platelets and coagulation factors and promotes leukocyte adherence. Over weeks and months, collagen is deposited as smooth muscle cells from the venous vessel wall migrate toward the tip. The rate of these processes varies among patients because of inherited or acquired characteristics. Ultimately, if clotting in excess of the endogenous fibrinolytic system's capacity develops, catheter thrombosis occurs.

There are several ways to restore patency to an existing catheter if it is decided that a new catheter placement at a different site may be delayed. Commonly, a catheter may be exchanged for a new catheter using guidewires as placeholders when the initial catheter is removed. The guidewires are generally advanced using fluoroscopic guidance, the catheter is then liberated from the body tissues and a new catheter is then advanced over the guidewire to the same location as the prior, occluded catheter. This method, although effective, requires patient sedation, access to a surgical or fluoroscopic suite and numerous hospital personnel, including at least one nurse and a physician. The major setback is that the catheter follows in the same tract as the prior catheter and it may be directed into the same fibrin sleeve that has formed.

SUMMARY

Dialysis catheter occlusion is a common problem affecting nearly every hemodialysis patenting who has one. Overall catheter patency rates are low, and catheter use in our system remains high creating increased healthcare costs and significant frustrations for those dialysis patients. A catheter occlusion will generally be discovered at the dialysis center and many times patients will need to go to the hospital for treatment prior to receiving dialysis. Once at the hospital thrombolytic medication can be injected at the entry port or patient can have the surgical or Interventional radiology teams exchange the catheter while sedated. While these methods have shown some success and are currently employed to restore patency, the described invention and method of use creates a much improved means of using the thrombolytic that speeds up lyses times and improved fibrin and clot removal.

The fibrin which can form all along the catheter causes occlusion once the fibrin sheath covers the distal tip. Generally, the inflow port of the catheter will be useable as an injection will displace the fibrin and allow fluid passage out of the catheter. The entry/blood aspiration/draw port however remains non-functional as the fibrin acts as a ball-valve mechanism not allowing blood to flow to the proximal catheter. The inner lumen volume of the dialysis catheter may be upwards of 2 ccs in each port. When thrombolytics are injected they diffuse through the 2 ccs and some of it reaches the tip and goes on to lyse the fibrin. Much of the thrombolytics however remains unused within the length of the catheter not coming into contact with the fibrin at the tip. The described invention is an innovative means of applying the thrombolytics directly at the catheter tip and can be utilized at the patient's bedside without the need for surgical suite or a large medical team.

A non-invasive means of restoring patency to a catheter is that of employing lytic therapy which has proven effective. This is performed by using a syringe to inject a thrombolytic medication such as TPA (Tissue Plasminogen Activator) directly into the proximal port of the catheter and allowed to "soak" in the catheter lumen to dissolve the fibrin sheath at the tip. This may be performed without use of imaging requiring only a nurse to perform. After 1-3 hrs., the catheter is checked for patency by aspiration using a syringe. The invention described relates to thrombolysis of catheter using more directed thrombolytic therapy.

The described innovation utilizes an intraluminal catheter placed with in the lumen of the dialysis catheter to apply directed thrombolysis at the tip where the largest thrombus burden exists. The catheter is created in specific sizes, or in one embodiment—a variable size in order to provide direct infusion. The design allows the user to match the need infusion length with the dialysis catheter size and precisely direct drug infusion at the exact point of need. The application can be performed in a non-surgical setting such as the ED or in the dialysis clinic with the need for only a chest x-ray for placement confirmation.

Although prior art describes the use of catheters for thrombolysis the presented invention creates a means to exploit the standard design of dialysis catheters in order to allow the user to apply the drug in precise location at the patient's bedside or in an outpatient setting such as a dialysis center. To further the utility of the invention means of length and quantity of drug administration are combined as the art combines and infusion module with the measured infusion catheter. The device uses either preloaded medication, or in a second embodiment, the medication is added to the device prior to its use. The invention is used as a disposable, self-contained system which can be matched to the appropriate dialysis catheter taken out of its packaging and either loaded with medication or preloaded then advanced into the patient's catheter, adjusted for medication duration and then turned on. Once the medication has been given, the catheter and system are removed, and the patient can then be dialyzed.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. Further, any of the elements and features disclosed herein may be combined in any manner with any of the other elements and features disclosed herein.

DESCRIPTION OF THE DRAWINGS

The components in the figures are not necessarily to scale, emphasis instead being placed upon illustrating the principles of the invention. In the figures, like reference numerals designate corresponding parts throughout the different views

FIG. 11 illustrates the components housed within the Infusion system, a medication reservoir and output catheter and the infusion controls with electronically controlled motor and pump mechanism and.

DETAILED DESCRIPTION

Hemodialysis patients require routine large volume blood exchange to survive and our bodies fight off efforts to allow this access. For many dialysis patients a permanent, indwelling catheter is the means of providing such access. Dialysis catheters have advantages over other methods of access however also have a limited time in which they will stay open and function mainly because of fibrin and clot forming on the tip. This invention and the method of use describe a means to direct a drug, a thrombolytic, directly at the point needed for a specific duration for dialysis catheters which are made in specific standard sizes.

Figure 1:
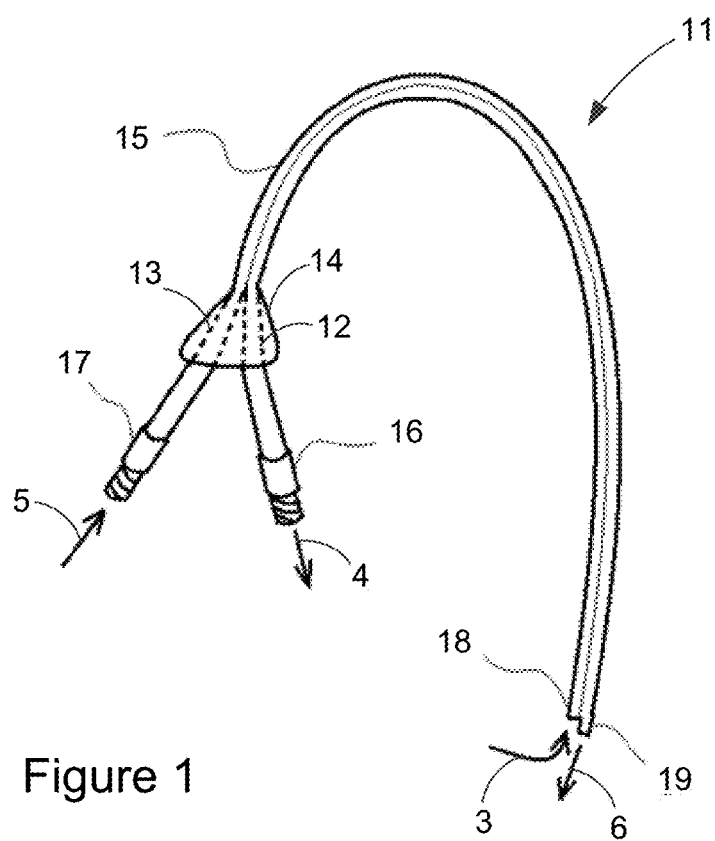
FIG. 1 illustrates a standard tunneled type dialysis catheter.

FIG. 1 illustrates a standard dialysis catheter 11 consisting of an aspiration tube 12, an injection tube 13 held together by a cuff 14 and a catheter 15. The aspiration tube 12 is attached to an aspiration port 16 on one end, and a distal tip on the other end. The injection tube 13 is attached to an injection port 17 on one end, and a distal tip on the other end. The arrows 3, 4, 5, 6 represent the direction of the blood flow. Specifically, the patient's blood exits the patient's body by entering 3 the distal tip of the aspiration tube 12, flowing through the aspiration tube 12, and exiting 4 the aspiration port 16 to become filtered. Once filtered, the patient's blood is returned to the patient's body by entering 5 through the injection port 17, flowing through the injection tube 13, and exiting 6 the distal tip of the injection tube 19.

Figure 2:
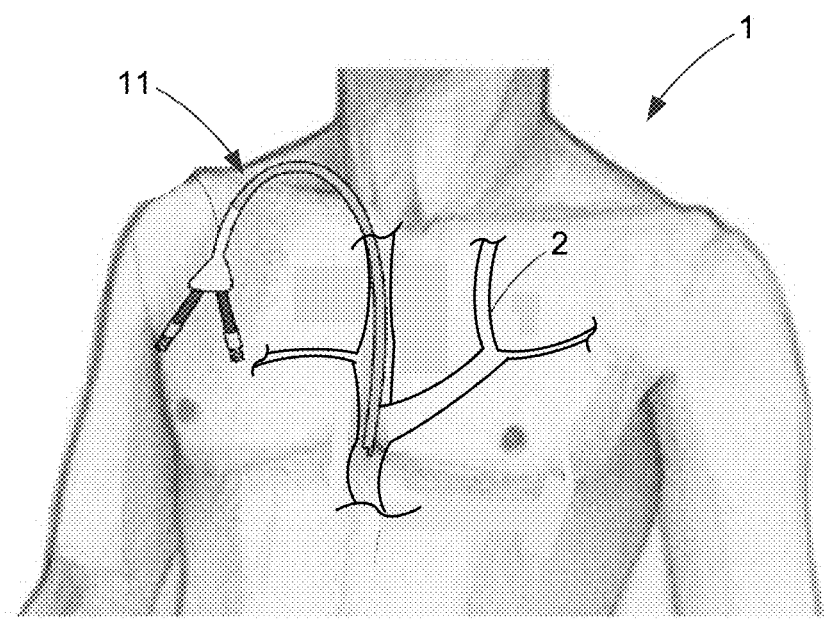
FIG. 2 illustrates a dialysis catheter with the distal tip positioned near the heart in the chest.

FIG. 2 illustrates the standard dialysis catheter 11 implanted in a patient's 1 chest near the heart, with the distal tips of the aspiration tube 18 and the injection tube 19 inserted into the patient's chest 1 superior vena cava blood vessel 2.

Figure 3:
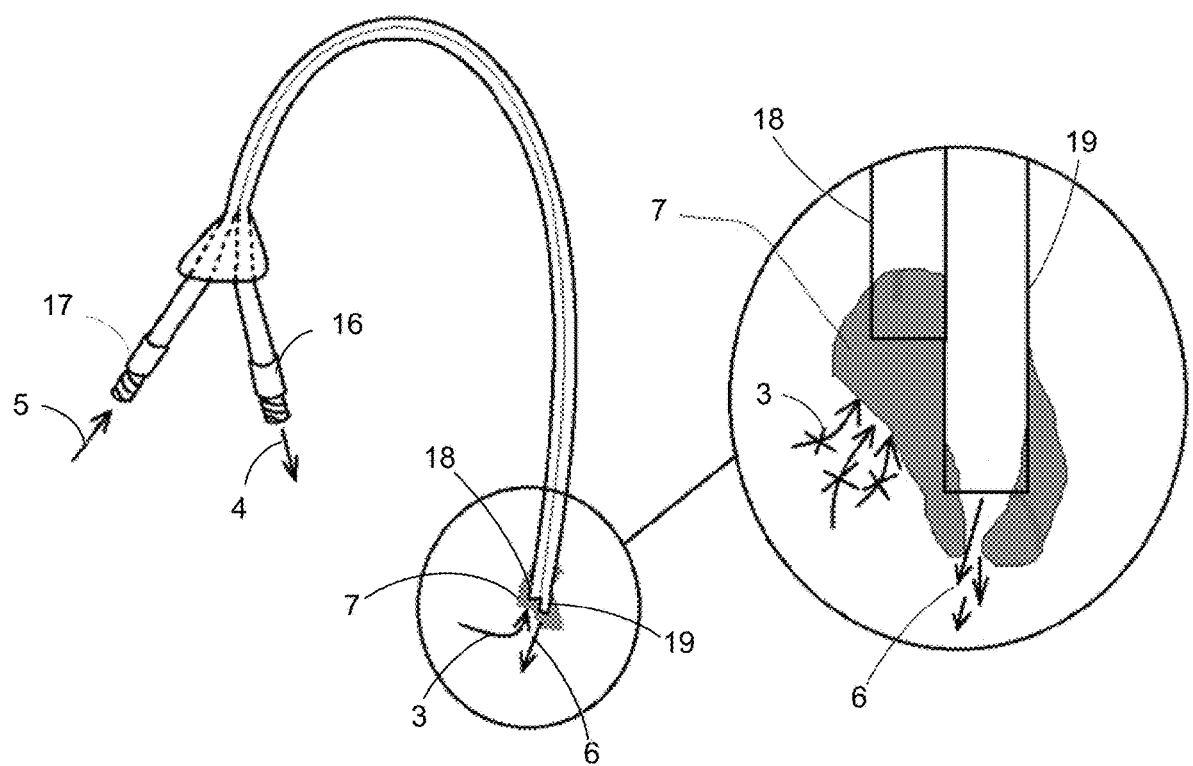
FIG. 3 illustrates an occluded dialysis catheter with development of fibrin and clot at the distal tip.

FIG. 3 illustrates how the fibrin and clot 7 developed on the distal tips of the aspiration tube 18 and the injection tube 19 restricting the flow of the patient's blood through the standard dialysis catheter 11. The patient's blood exiting 6 the distal tip of the injection tube 19 may be able to break the fibrin and clot 7 forming around the distal tip of the injection tube 19 due to pressure. However, the patient's blood entering 3 the distal tip of the aspiration tube 18 cannot pass through the fibrin and clot 7 forming around the distal tip of the aspiration tube 18 due to the ball-valve mechanism.

Figure 4:
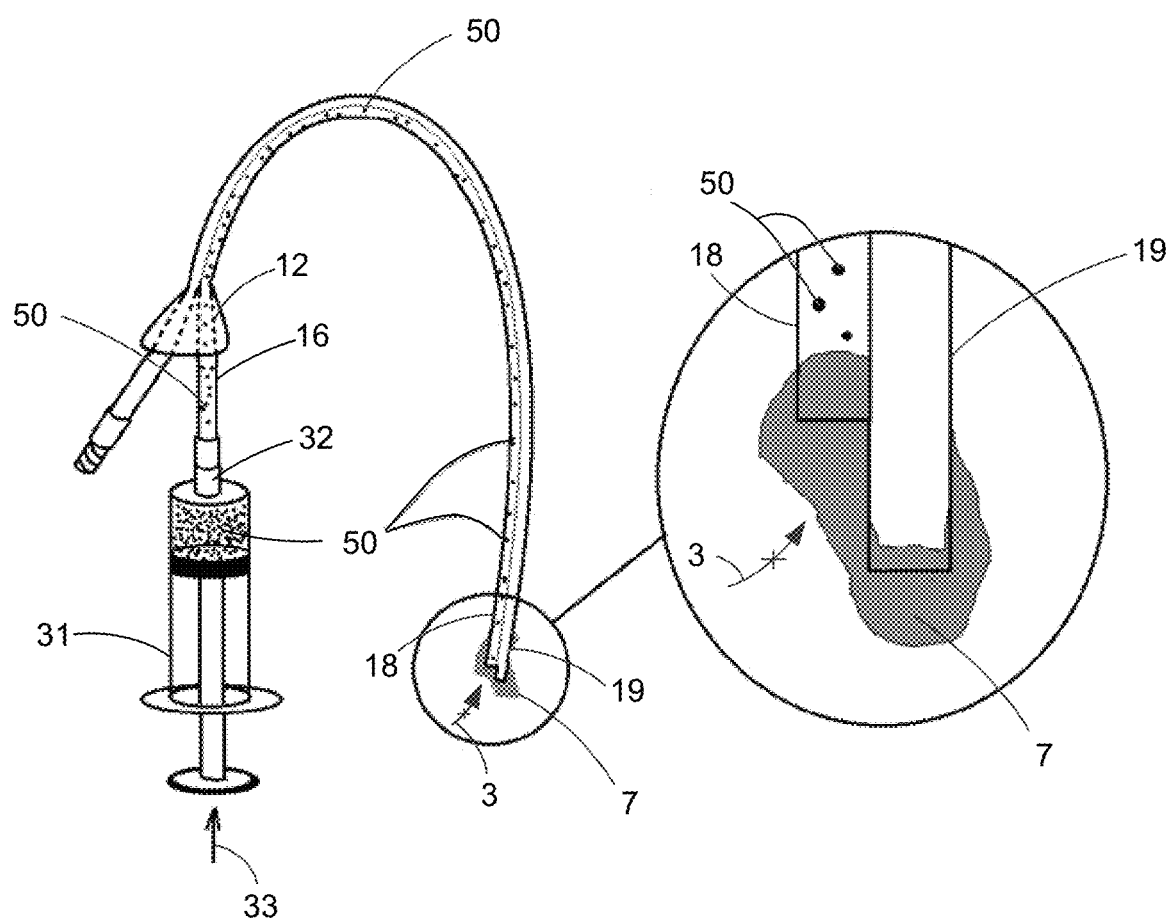
FIG. 4 illustrates an injection of medication into the dialysis catheter port with medication diffusion to the tip.

FIG. 4 illustrates the standard method of restoring patency in the standard dialysis catheter 11. A syringe 31 containing medication 50 attaches to the aspiration port 16 using a standard luer lock attachment 32. The syringe 31 injects 33 the medication 50 in the aspiration port 16. Pressure from the injection 33 pushes the medication 50 into the aspiration tube 12. This method intends the medication 50 to reach the distal tip of the aspiration tube 18, where the medication 50 breaks down the fibrin and clot 7 to allow the patient's blood to enter 3 the distal tip of the aspiration tube 18. However, this method is ineffective because the injection 33 does not produce enough pressure, resulting in most of the injected medication 50 to remain in the aspiration tube 12 without reaching the distal tip of the aspiration tube 18. The small amount of medication 50 reaching the distal tip of the aspiration tube 18 is not sufficient to break down enough fibrin and clot 7 to allow the patient's blood to enter 3 the distal tip of the aspiration tube 18.

Figure 5:
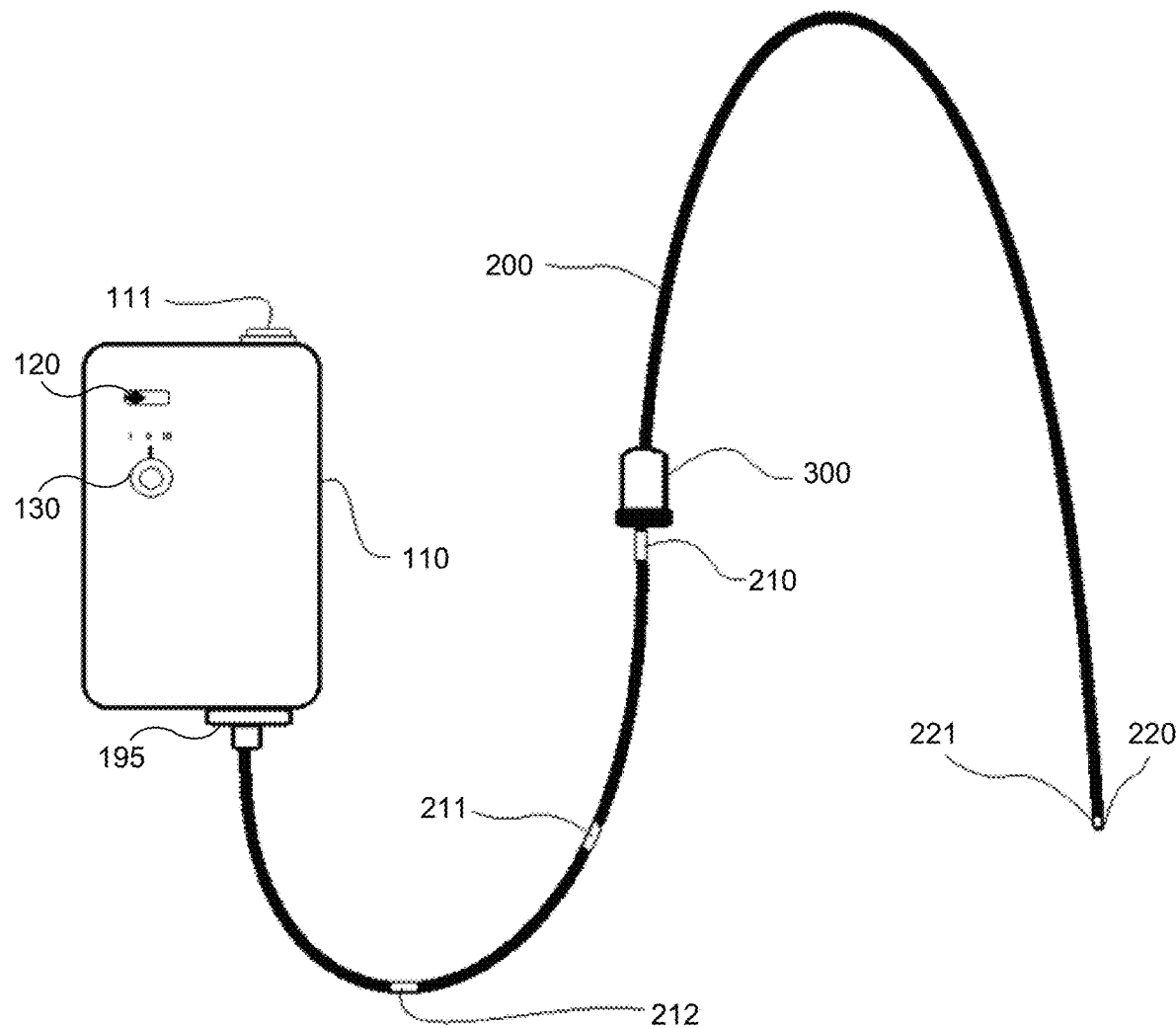
FIG. 5 illustrates the infusion system with the infusion pump and control 100 and the preset infusion catheter and the associated components.

FIG. 5 illustrates an embodiment of the catheter clearance device 100, consisting of a catheter clearance box 110 connected to a medication injection port 111 on one end, and an infusion catheter connector 195 on the other end. The infusion catheter connector 195 connects the catheter clearance box 110 to an infusion catheter 200.

The infusion catheter 200 is connected to the catheter clearance box 110 on one end and has a distal tip on the other end. A connector and valve 300 attaches to the infusion catheter 200. The infusion catheter 200 displays placement markers measuring 19 centimeters 210, 23 centimeters 211, and 27 centimeters 212 respectively from the distal tip of the infusion catheter 220. The distal tip of the infusion catheter 220 contains a radiopaque marker 221, which can be detected by x-ray.

A port switch 120 on the catheter clearance box 110 turns the catheter clearance device 100 on and off. A flow rate control selector 130 on the catheter clearance box 110 controls the speed at which medication travels from the catheter clearance box 110 to the distal tip of the infusion catheter 220.

Figure 6:
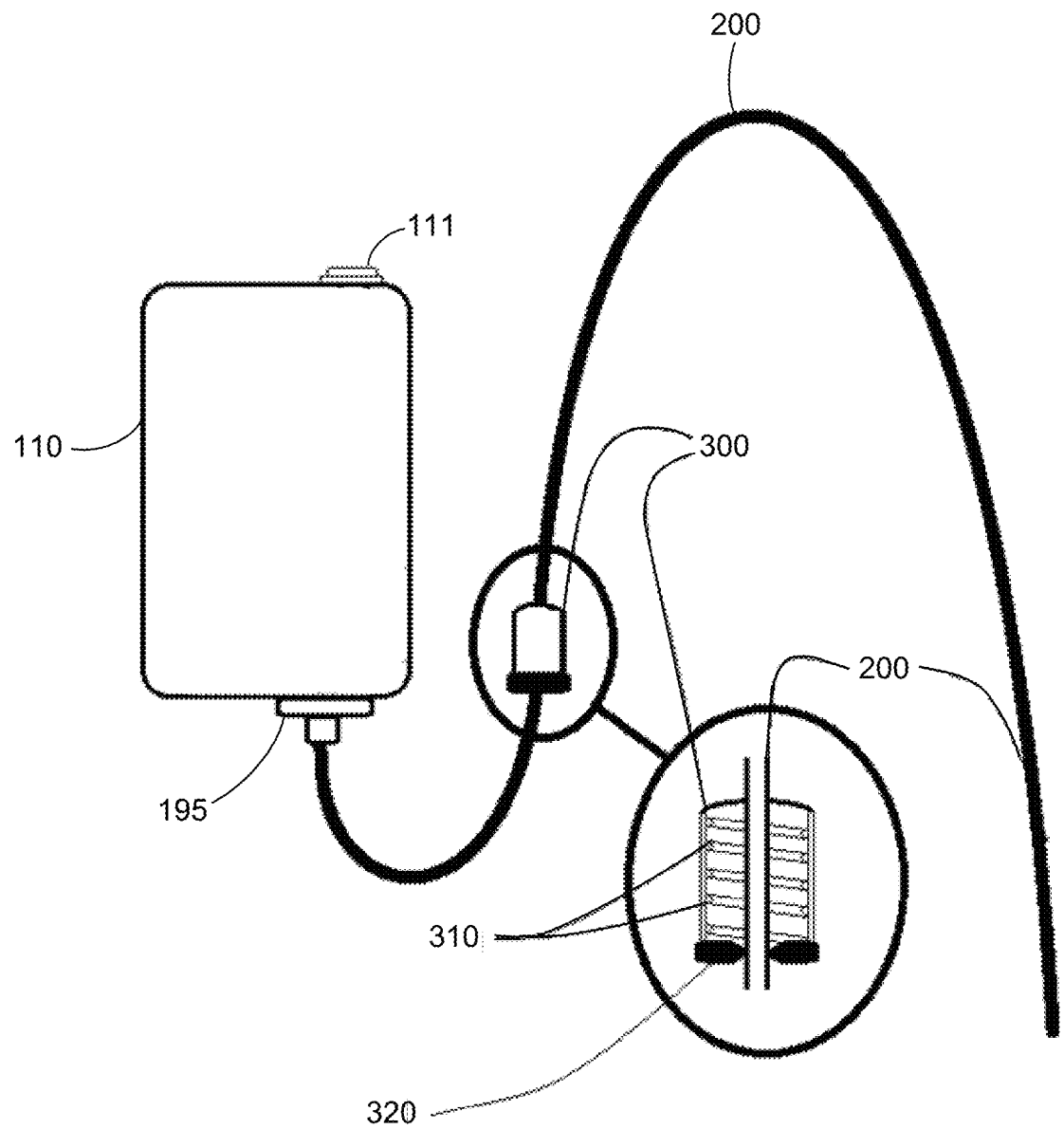
FIG. 6 illustrates an anti-leak connector with internal luer lock connector 310 and anti-leak valve sealing around the infusion catheter.

FIG. 6 illustrates the connector and valve 300, which is attached to the infusion catheter 200 and can be moved along the length of the infusion catheter 200 for proper placement of the infusion catheter 200 inside standard dialysis catheters. The connector and valve 300 consists of a female luer lock connector 310 and an anti-leak valve 320. The female luer lock connector 310 can attach to the aspiration port 16 of a standard dialysis catheter 11. The anti-leak valve 320 can seal the outer portion of the infusion catheter 200. When fully sealed, the anti-leak valve 320 prevents the flow of medication inside the infusion catheter 200 from escaping, thus directing the medication to the clot.

Figure 7:
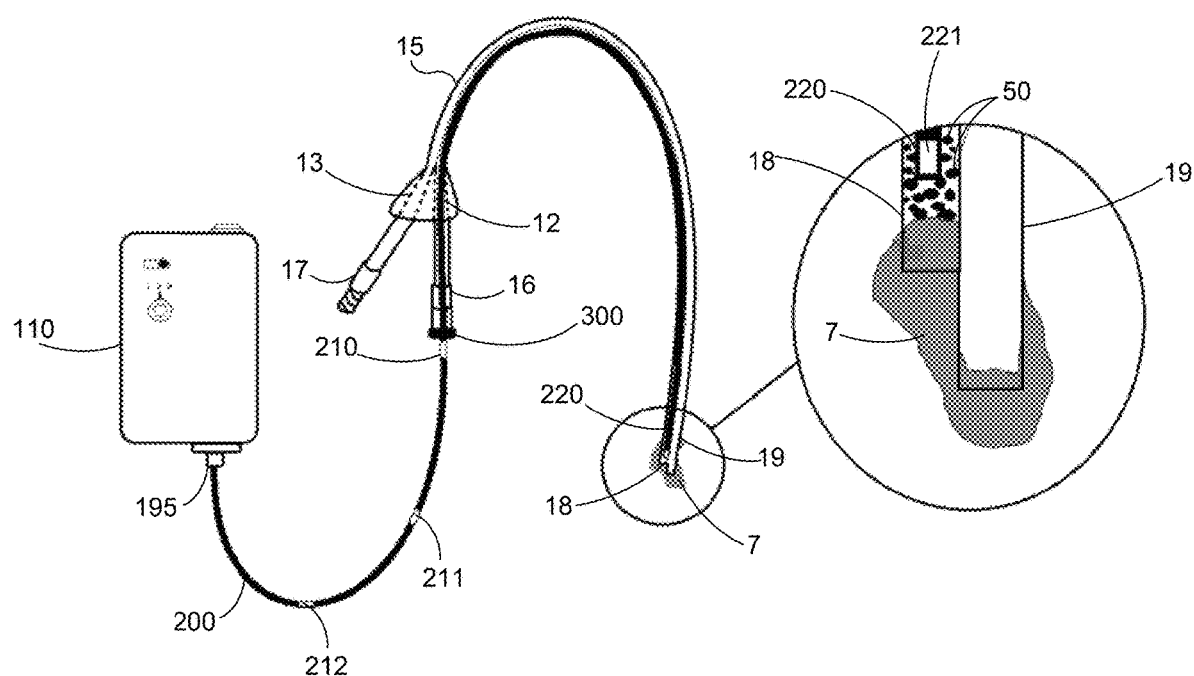
FIG. 7 illustrates an infusion system deployed with the tip in the dialysis catheter and medication infused directly at the dialysis catheter tip.

FIG. 7 illustrates the placement of the catheter clearance device 100 inside the aspiration tube 12 of a standard dialysis catheter 11. Specifically, the infusion catheter 200 is inserted into the catheter 15 of the standard dialysis catheter 11 through the aspiration port 16. The catheter clearance device 100 is correctly placed inside a standard dialysis catheter 11 when the distal tip of the infusion catheter 220 reaches the distal tip of the aspiration tube 18. In this illustration, the first placement marker 210 confirms this correct placement when the placement marker 210 is positioned directly underneath the aspiration port 16 of the standard dialysis catheter 11. The correct placement can also be confirmed by an x-ray showing the radiopaque marker 221 is aligned with the distal tip of the aspiration tube 18 of the standard dialysis catheter 11. The connector and valve 300 attaches to the aspiration port 16 to secure the infusion catheter 200 inside the catheter 15 of the standard dialysis catheter 11 once correct placement is confirmed. The catheter clearance device 100 can also be placed inside the injection tube 13 of the standard dialysis catheter 11 using the same method described above.

Figure 8:
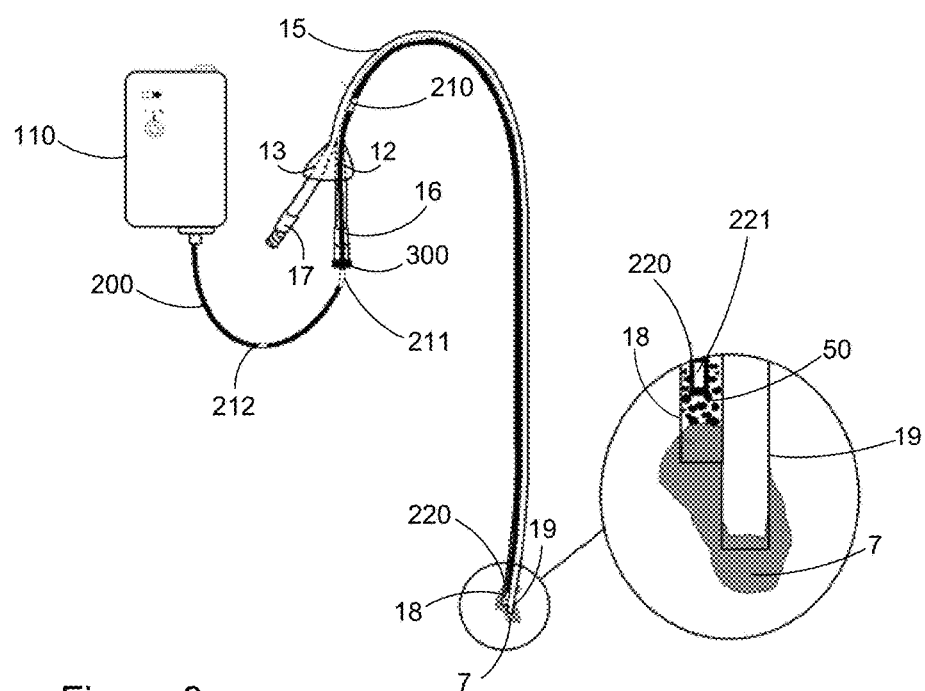
FIG. 8 illustrates the infusion system deployed within a longer dialysis catheter confirmed by the matched infusion catheter marker.

FIG. 8 illustrates the placement of the catheter clearance device 100 inside a standard dialysis catheter 11 with a longer catheter 15, such that the infusion catheter 200 is advanced until the second placement marker 211.

Figure 9:
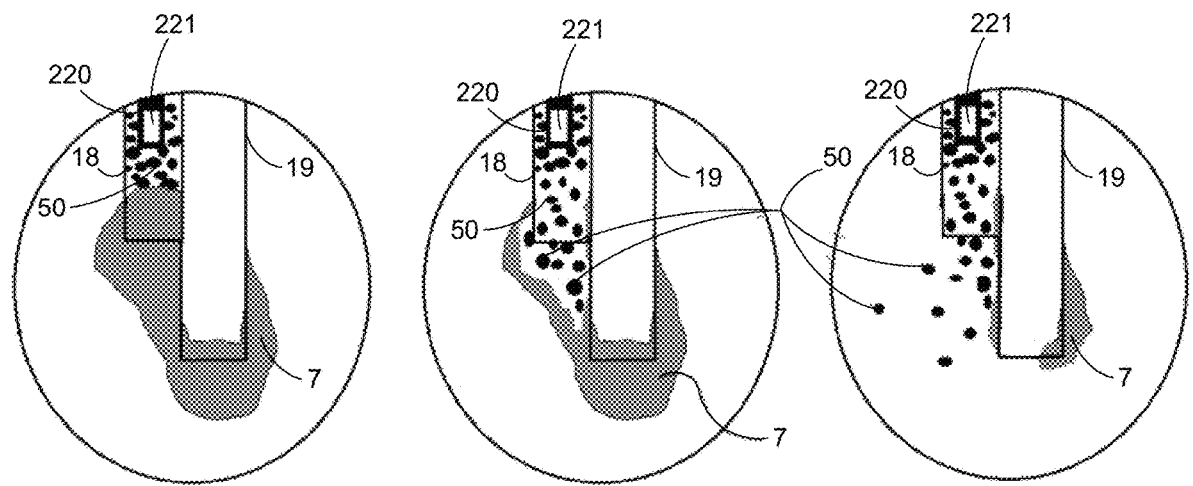
FIG. 9 illustrates the lysis process, from left to right wherein the medication dissolves the fibrin and clot and restored catheter patency.

FIG. 9 the infusion of the medication 50 to the distal tip of the aspiration tube 18 of the standard dialysis catheter 11. The distal tip of the infusion catheter 220 ensures delivery of all injected medication 50 directly to the distal tip of the aspiration tube 18. Thus, there will be sufficient medication 50 to dissolve the fibrin and clot 7, restoring patency to the standard dialysis catheter 11.

Figure 10:
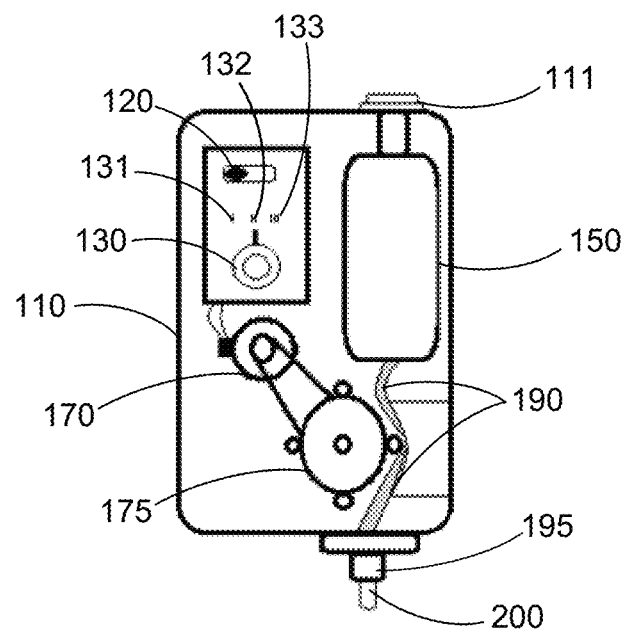
FIG. 10 illustrates an inside view of the infusion pump system with internal components visualized.

FIG. 10 illustrates the interior of the catheter clearance box 110. The medication injection port 111 at the top of the catheter clearance box 110 is connected to a medication reservoir 150. In one embodiment of the invention, the medication reservoir 150 is made of an evacuated compliant sac structure that expands as it accepts fluids. This embodiment eliminates air in the system. The other end of the medication reservoir 150 is connected to an outflow line 190. The other end of the outflow line 190 is connected to the infusion catheter connector 195. The infusion catheter 200 attaches to the other end of the infusion catheter connector 195.

The port switch 120 is connected to the motor 170. The motor is connected to the belt and infusion gear 175.

The flow rate control selector 130 displays three flow rate options on the exterior of the catheter clearance box 110. The three respective flow rate options are minimum 131, medium 132, and maximum 133. On the interior of the catheter clearance box 110, the flow rate control selector 130 is connected to the motor 170.

Figure 11:
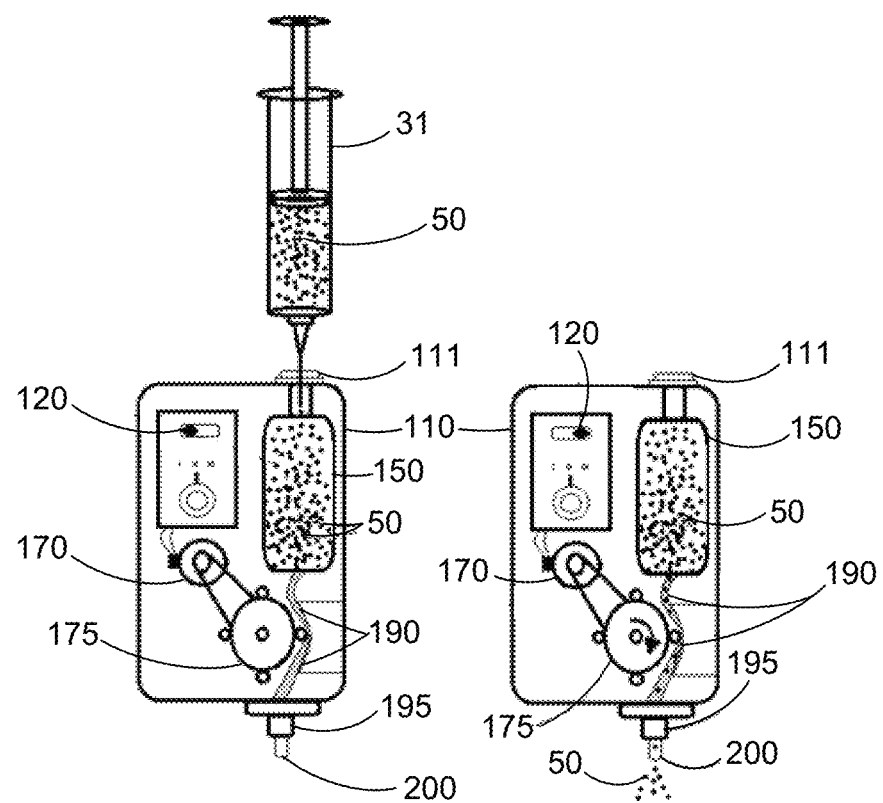

FIG. 11 illustrates how medication 50 travels through the catheter clearance box 110. Specifically, a syringe 31 injects 33 medication 50 through the medication injection port 110. The medication 50 then flows into the medication reservoir 150.

When the port switch 120 is on, the motor 170 powers the belt and infusion gear 175 to rotate. The belt and infusion gear 175 pushes the medication 50 in the medication reservoir 150 through the outflow line 190 to the infusion catheter connector 195, where the medication 50 flows into the infusion catheter 200.

Figure 12:
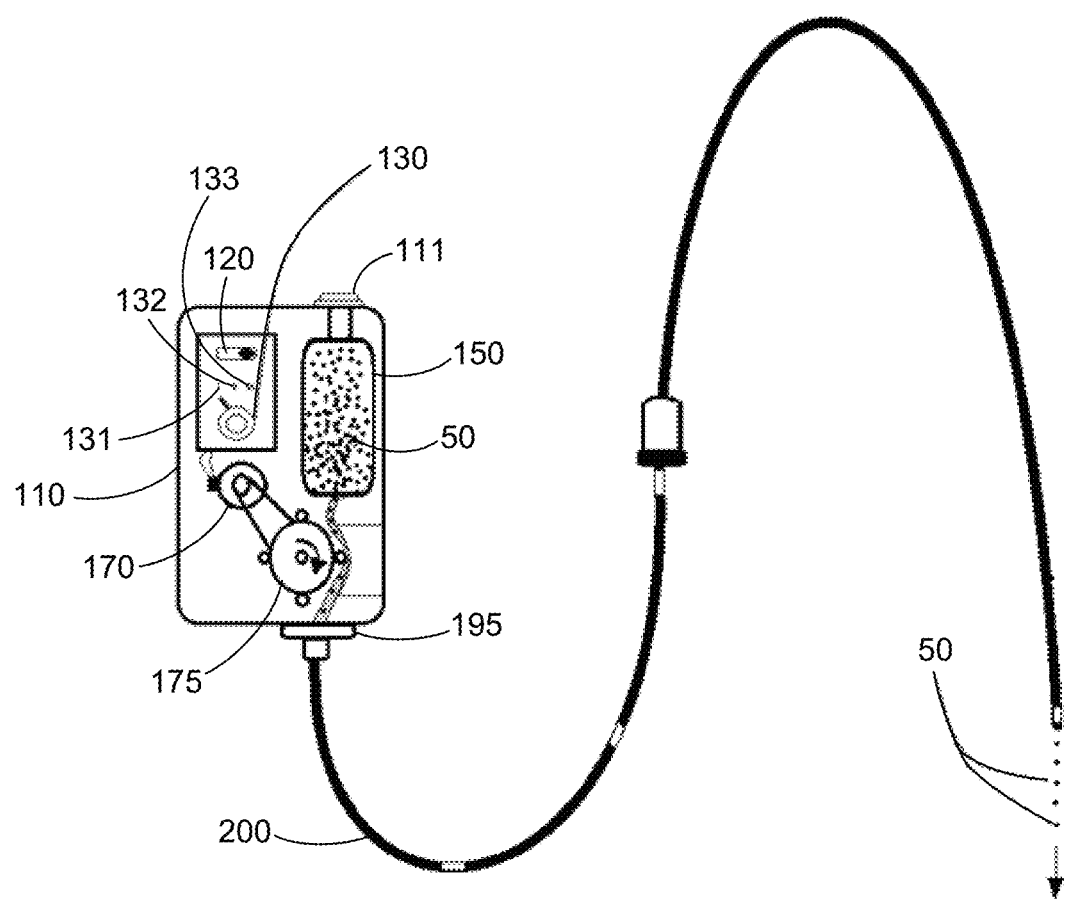
FIG. 12 illustrates a flow rate control sensory set on low with minimal medication output.

FIG. 12 illustrates the catheter clearance device 100 operating on minimum 131. Specifically, when the flow rate control selector 130 is set to minimum 131 and the port switch 120 is on, the motor 170 powers the belt and infusion gear 175 that rotates at a slow speed. As a result, the medication in the medication reservoir 150 is slowly pushed into the outflow line 190, then through the infusion catheter connector 195 into the infusion catheter 200, eventually reaching the distal tip of the infusion catheter 220 and exiting the infusion catheter 200 at a slow rate.

Figure 13:
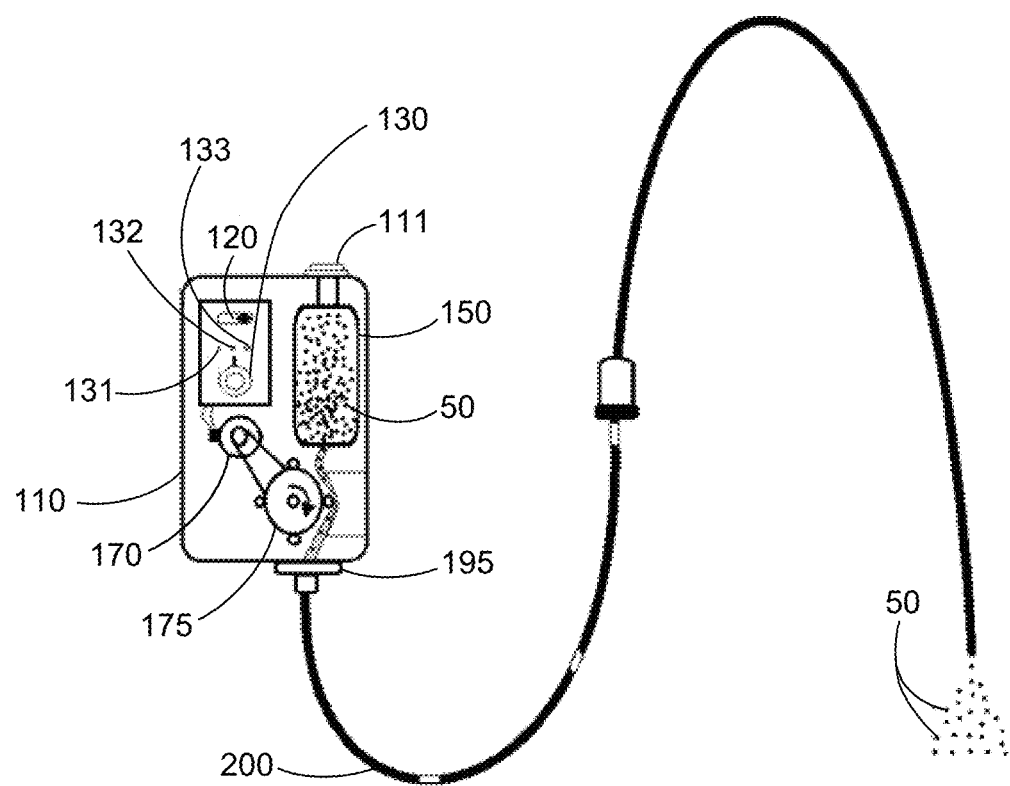
FIG. 13 illustrates a flow rate control sensory set on medium with moderate medication output.

FIG. 13 illustrates the catheter clearance device 100 operating on medium 132. Specifically, when the flow rate control selector 130 is set to medium 132 and the port switch 120 is on, the motor 170 powers the belt and infusion gear 175 that rotates at a medium speed. As a result, the medication in the medication reservoir 150 is pushed into the outflow line 190 at a medium speed, then through the infusion catheter connector 195 into the infusion catheter 200, eventually reaching the distal tip of the infusion catheter 220 and exiting the infusion catheter 200 at a medium rate. The medication may exit the infusion catheter through a nozzle, which may comprise any type opening at the distal end of the infusion catheter through which medication pass out of the infusion catheter 200.

Figure 14:
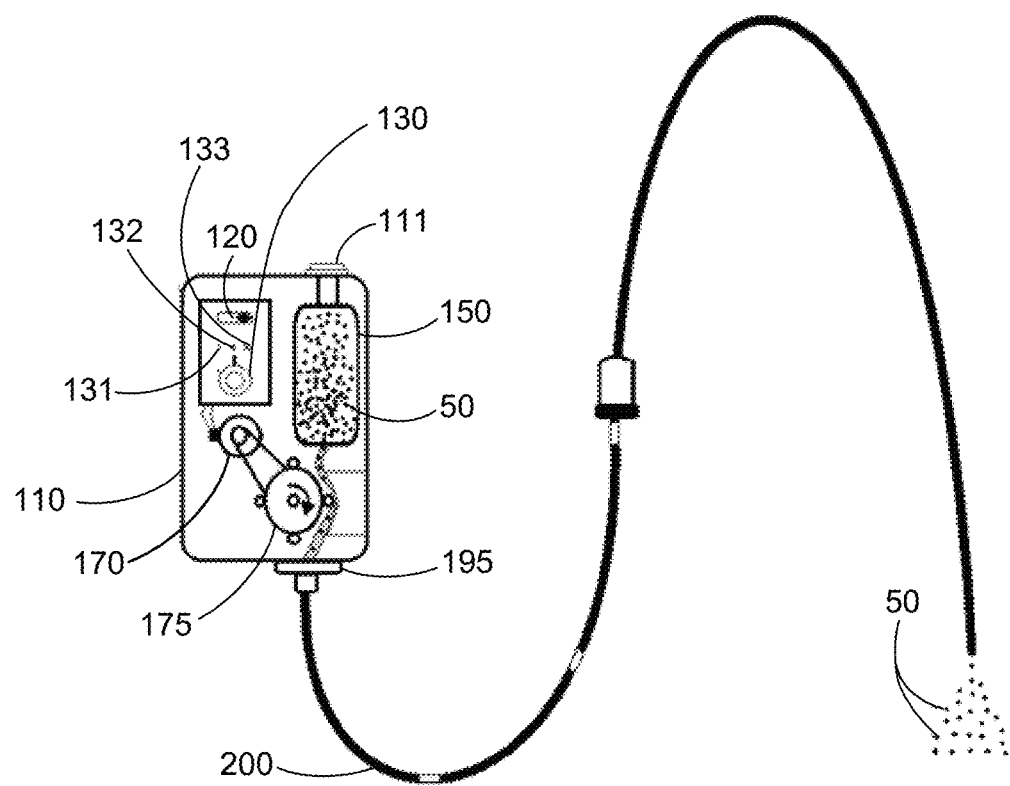
FIG. 14 illustrates a flow rate control sensory set on high with maximum medication output.

FIG. 14 illustrates the catheter clearance device 100 operating on maximum 133. Specifically, when the flow rate control selector 130 is set to maximum 133 and the port switch 120 is on, the motor 170 powers the belt and infusion gear 175 that rotates at a high speed. As a result, the medication in the medication reservoir 150 is pushed into the outflow line 190 at a high speed, then through the infusion catheter connector 195 into the infusion catheter 200, eventually reaching the distal tip of the infusion catheter 220 and exiting the infusion catheter 200 at a fast rate.

Figure 15:
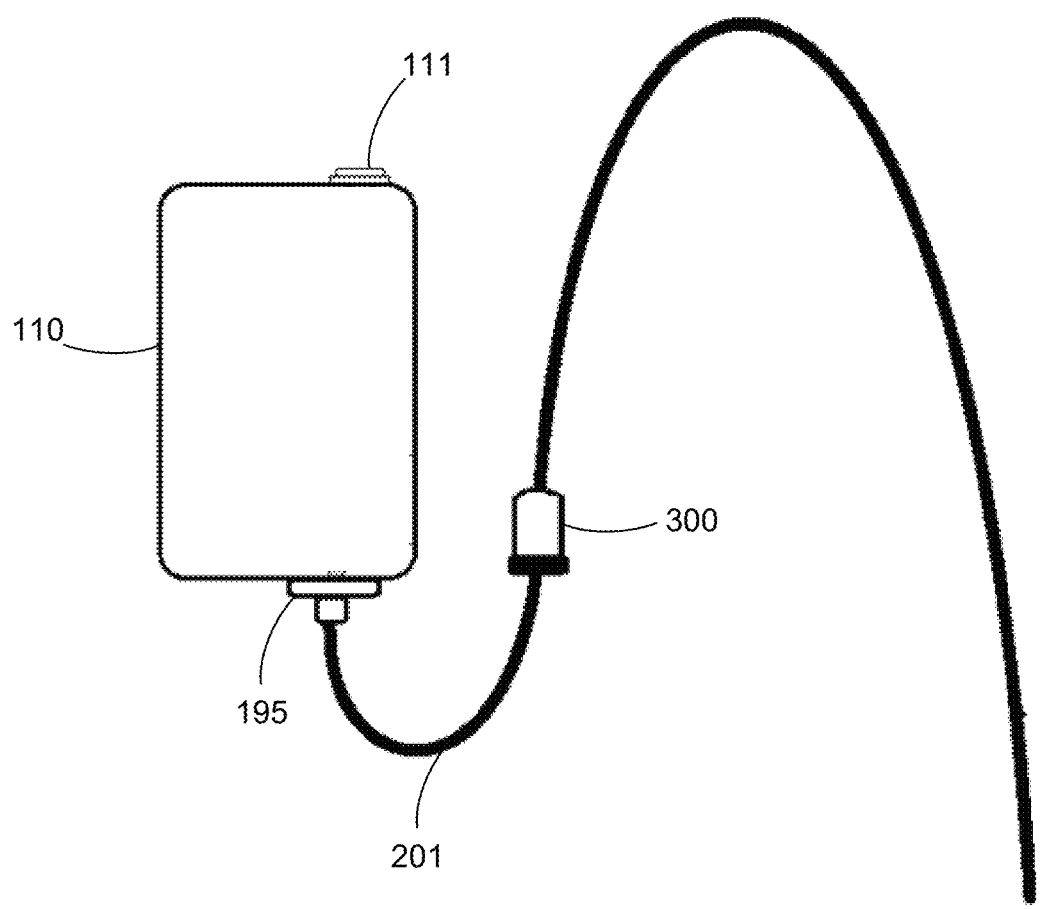
FIG. 15 illustrates an additional embodiment of the infusion system with a predetermined, non-adjustable catheter length and anti-leak connecter.

FIG. 15 illustrates another embodiment of the catheter clearance device 100 using a premeasured infusion catheter 201, which does not display placement markers 210, 211, 212. The placement of the connector and valve 300 is preset such that the connector and valve 300 cannot move along the infusion catheter 200. Such infusion catheters 200 vary in length and are based on the length of catheters on standard dialysis catheters 11. Using this embodiment, the user would choose the appropriate length of a premeasured infusion catheter 201 to insert into the infusion catheter connector 195.

Figure 16:
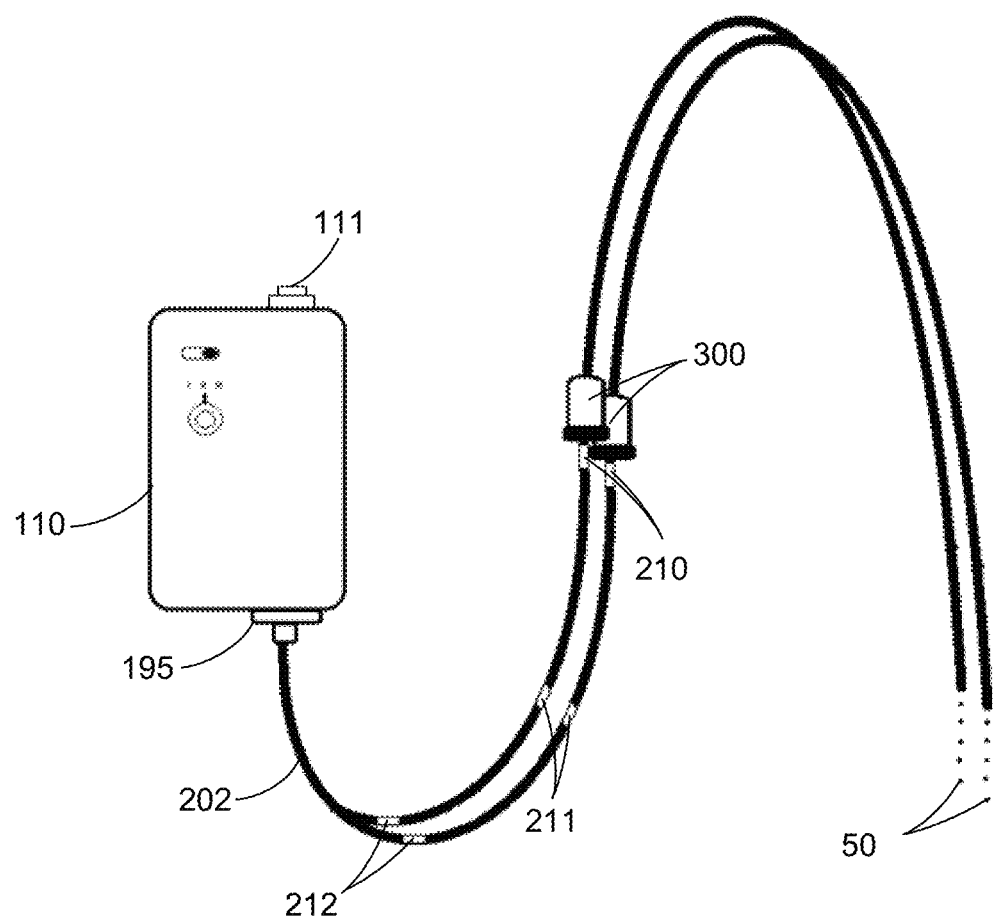
FIG. 16 illustrates an additional embodiment of the infusion system with two outflow catheters.

FIG. 16 illustrates another embodiment of the catheter clearance device 100 where a 2-prong infusion catheter 202 is attached to the infusion catheter connector 195. The 2-prong infusion catheter 202 splits into two tubes, each tube displaying three placement markers 210, 211, 212. A connector and valve 300 is attached to each tube. This embodiment allows the catheter clearance device 100 to be placed inside both the aspiration tube 12 and the injection of a standard dialysis catheter 11, such that a single catheter clearance device 100 can remove fibrin and clot 7 at the distal tips of the aspiration tube 18 and the injection tube 13 of the standard dialysis catheter 11 simultaneously.

Figure 17:
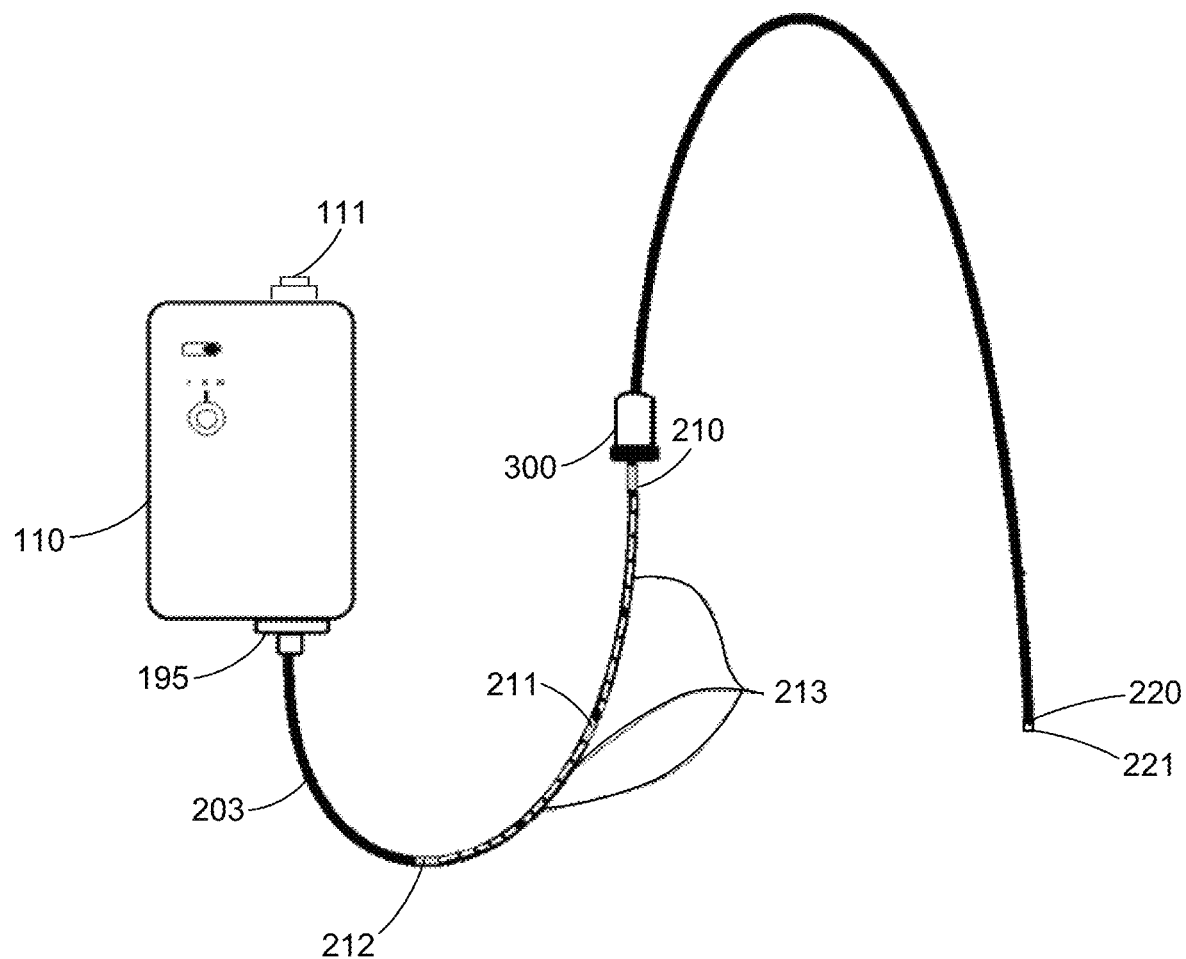
FIG. 17 illustrates an additional embodiment of the infusion system with measurement markers along the proximal infusion catheter.

FIG. 17 illustrates another embodiment of the catheter clearance device 100 where an Infusion catheter with measuring marks 203 is attached to the infusion catheter connector 195. In this embodiment, measuring marks 213 are displayed between the placement markers 210, 211, 212 such that the catheter clearance device 100 can restore the patency of dialysis catheters with non-standard length catheters. The measuring marks 213 may also help adjust the placement of the Infusion catheter 220 inside the catheter 15 of a standard dialysis catheter 11, should an x-ray of the radiopaque marker 221 indicate the radiopaque marker 221 is not fully aligned with the distal tip of the aspiration tube 18 or the injection tube 13 of a standard dialysis catheter 11.

Figure 18:
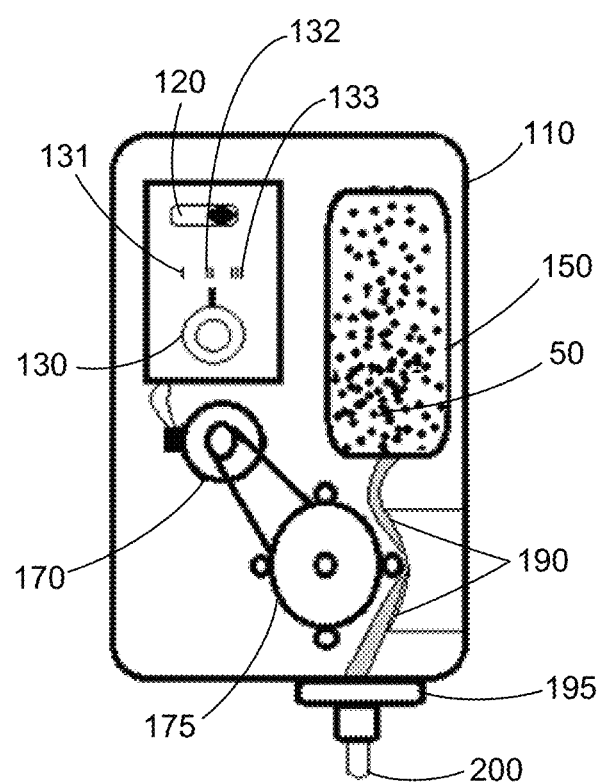
FIG. 18 illustrates an infusion system that is preloaded with a dose of the medication therefore not requiring the infusion port.

FIG. 18 illustrates another embodiment of the catheter clearance device 100 with no medication injection port 111 on the catheter clearance box 110. In this embodiment, the medication reservoir 150 is preloaded with medication 50. This embodiment allows the user to utilize the catheter clearance device 100 without the need to manually inject 33 medication 50 into the catheter clearance box 110.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A blood dialysis catheter clearance device for clearing a dialysis catheter comprising:
    a medication injection device comprising:
        a catheter clearance box having a first end and a second, opposite end;
        a medication reservoir disposed internal with respect to the catheter clearance box and connected to or configured as part of the medication injection device, the medication reservoir configured to contain medication which is to be provided to a patient, the medication reservoir having a first end configured to receive the medication in a first direction therethrough, and a second, opposite end having a wall through which the medication is configured to exit the medication reservoir in a second direction, the medication reservoir being made of an evacuated compliant sac structure that is configured to expand responsive to accepting medication in order to eliminate air in the device;
        only one single outflow line, having only one single inner lumen configured to contain the medication, having a first end and a second end, the first end of the outflow line being connected to an output port of the medication reservoir;
        an infusion catheter connector connected to the second end of the outflow line and configured to connect to an infusion catheter;
        a motor and infusion assembly disposed internal with respect to the catheter clearance box, the motor and infusion assembly comprising a motor and a belt and infusion gear, the belt and infusion gear being configured to be powered by the motor and engage with the outflow line to push the medication contained in the outflow line in a third direction parallel to the first and second directions so that the medication can be pushed out of the infusion catheter connector and into the infusion catheter, wherein the first, second, and third directions are all from the first end of the catheter clearance box to the second end thereof; and
        a medication injection port connected to the catheter clearance box and configured to direct the medication from a syringe into the medication reservoir, wherein the medication injection port is connected to a first side of the catheter clearance box, wherein the infusion catheter connector is connected to a second side of the catheter clearance box, and wherein the first side is disposed opposite and distal the second side;
    the infusion catheter having a first end and a second end, the first end of the infusion catheter connected to the infusion catheter connector to receive the medication, and the second end of the infusion catheter having a distal tip with a nozzle through which the medication exits the infusion catheter, the infusion catheter also having two or more placement markers which are visible on a portion of the infusion catheter that is outside of the dialysis catheter to provide location information of the distal tip without use of radiation during placement of the infusion catheter.

2. The dialysis catheter clearance device of claim 1 wherein the medication injection device comprises a port switch, a flow rate control selector, the motor, the belt and infusion gear, the medication reservoir, and the infusion catheter connector;
    the port switch connected to the motor;
    the flow rate control selector also connected to the motor; and
    the motor connected to the belt and infusion gear.

3. The blood dialysis catheter clearance device of claim 1 wherein the infusion catheter is configured as a premeasured length which corresponds to dialysis catheter sizes.

4. The blood dialysis catheter clearance device of claim 3 wherein the premeasured length of the infusion catheter is adjustable.

5. The blood dialysis catheter clearance device of claim 2 wherein the infusion catheter connector is a luer lock connector.

6. The blood dialysis catheter clearance device of claim 1 wherein the medication injection device further comprises the syringe.

7. The blood dialysis catheter clearance device of claim 1 wherein the two or more placement markers on the infusion catheter correspond to lengths of one or more dialysis catheters.

8. The blood dialysis catheter clearance device of claim 1 wherein the nozzle is configured to establish a different medication outflow pattern based on a medication flow rate.

9. The blood dialysis catheter clearance device of claim 1 further comprising an anti-leak valve through which the infusion catheter can be placed into the dialysis catheter.

10. The blood dialysis catheter clearance device of claim 1, wherein the belt and infusion gear comprises a body and a plurality of protrusions extending outwardly from the body, and wherein the plurality of protrusions are each configured to engage with the outflow line to push the medication contained in the outflow line in the third direction out of the infusion catheter connector and into the infusion catheter.

11. The blood dialysis catheter clearance device of claim 1, wherein the outflow line is disposed entirely internal with respect to the catheter clearance box.

12. The blood dialysis catheter clearance device of claim 1, wherein the medication reservoir extends from the medication injection port to the outflow line.

\* \* \* \* \*